United States Patent
Blaschke et al.

(10) Patent No.: US 7,543,481 B2
(45) Date of Patent: Jun. 9, 2009

(54) FLUID TESTING SENSOR HAVING VENTS FOR DIRECTING FLUID FLOW

(75) Inventors: Christina Blaschke, White Pigeon, MI (US); Daniel V. Brown, Elkhart, IN (US); Sung-Kwon Jung, Granger, IN (US)

(73) Assignee: Bayer Healthcare, LLC, Tarrytown, NY (US)

( * ) Notice: Subject to any disclaimer, the term of this patent is extended or adjusted under 35 U.S.C. 154(b) by 214 days.

(21) Appl. No.: 10/590,838

(22) PCT Filed: Feb. 4, 2005

(86) PCT No.: PCT/US2005/003624

§ 371 (c)(1),
(2), (4) Date: Aug. 24, 2006

(87) PCT Pub. No.: WO2005/078436

PCT Pub. Date: Aug. 25, 2005

(65) Prior Publication Data

US 2007/0062262 A1    Mar. 22, 2007

Related U.S. Application Data

(60) Provisional application No. 60/542,348, filed on Feb. 6, 2004.

(51) Int. Cl.
*G01N 33/487* (2006.01)
*G01N 27/403* (2006.01)

(52) U.S. Cl. ............. 73/61.41; 204/403.01; 204/403.03

(58) Field of Classification Search ............... 73/61.41; 204/403.01, 403.03, 403.11
See application file for complete search history.

(56) References Cited

U.S. PATENT DOCUMENTS

| | | | |
|---|---|---|---|
| 5,120,420 A | 6/1992 | Nankai et al. |
| 5,194,393 A | 3/1993 | Hugl et al. |
| 5,320,732 A | 6/1994 | Nankai et al. |
| 5,336,388 A | 8/1994 | Leader et al. |
| 5,437,999 A | 8/1995 | Diebold et al. |
| 5,460,968 A | 10/1995 | Yoshida et al. |
| 5,518,689 A | 5/1996 | Dosmann et al. |
| 5,582,697 A | 12/1996 | Ikeda et al. |

(Continued)

FOREIGN PATENT DOCUMENTS

EP    0 537 761    10/1992

(Continued)

OTHER PUBLICATIONS

PCT International Search Report dated Sep. 13, 2005, for International Application No. PCT/US2005/003624 (4 pages).

(Continued)

*Primary Examiner*—Daniel S Larkin
(74) *Attorney, Agent, or Firm*—Nixon Peabody LLP

(57) ABSTRACT

A sensor for analyzing a fluid sample has a sample cavity for accepting sample fluid. At least one test region is disposed along the sample cavity, and at least one vent fulfills the dual function of venting the sample cavity and guiding the sample fluid in the sample cavity via appropriate location and geometry of at least one sample guide edge.

30 Claims, 5 Drawing Sheets

U.S. PATENT DOCUMENTS

| | | | |
|---|---|---|---|
| 5,611,999 | A | 3/1997 | Dosmann et al. |
| 5,628,890 | A | 5/1997 | Carter et al. |
| 5,660,791 | A | 8/1997 | Brenneman et al. |
| 5,676,811 | A | 10/1997 | Makino et al. |
| 5,755,953 | A | 5/1998 | Henning et al. |
| 5,759,364 | A | 6/1998 | Charlton et al. |
| 5,798,031 | A | 8/1998 | Charlton et al. |
| 5,846,392 | A | 12/1998 | Knoll |
| 5,866,349 | A | 2/1999 | Lilja et al. |
| 5,997,817 | A | 12/1999 | Crismore et al. |
| 6,004,441 | A | 12/1999 | Fujiwara et al. |
| 6,036,919 | A | 3/2000 | Thym et al. |
| 6,129,823 | A | 10/2000 | Hughes et al. |
| 6,143,164 | A | 11/2000 | Heller et al. |
| 6,254,736 | B1 | 7/2001 | Earl et al. |
| 6,270,637 | B1 | 8/2001 | Crismore et al. |
| 6,531,040 | B2 | 3/2003 | Musho et al. |
| 6,540,891 | B1 | 4/2003 | Stewart et al. |
| 6,841,052 | B2 | 1/2005 | Musho et al. |
| 7,122,102 | B2 | 10/2006 | Wogoman |
| 7,125,481 | B2 | 10/2006 | Musho et al. |
| 7,138,041 | B2 | 11/2006 | Su et al. |
| 2004/0007461 | A1 | 1/2004 | Edelbrock et al. |
| 2004/0194302 | A1 | 10/2004 | Bhullar et al. |
| 2004/0253367 | A1 | 12/2004 | Wogoman |
| 2005/0183953 | A1 | 8/2005 | Su et al. |
| 2005/0224345 | A1 | 10/2005 | Taniike et al. |
| 2006/0070878 | A1 | 4/2006 | Wu et al. |

FOREIGN PATENT DOCUMENTS

| | | |
|---|---|---|
| EP | 0 538 830 | 10/1992 |
| EP | 1 413 879 | 4/2004 |
| JP | 5-126745 | 5/1993 |
| JP | 5-256811 | 10/1993 |
| WO | WO 03/012421 | 2/2003 |

OTHER PUBLICATIONS

PCT Written Opinion dated Sep. 13, 2005 for International Application No. PCT/US2005/003624 (5 pages).

FLUID TESTING SENSOR HAVING VENTS FOR DIRECTING FLUID FLOW

CROSS-REFERENCE TO RELATED APPLICATION

This application claims priority to Application No. 60/542,348, filed on Feb. 6, 2004, which is incorporated by reference in its entirety.

FIELD OF THE INVENTION

The present invention relates generally to sensors for fluid analysis and more particularly is directed to sensors having vents placed for controlling fluid location within a capillary cavity.

BACKGROUND OF THE INVENTION

Sensors are useful for measuring analytes in many applications, including clinical, environmental, and process monitoring. In many of these applications, it is desirable to perform the measurement using a small liquid sample volume. Correct positioning of the sample aliquot over the transducer element or reactive area of the sensor is crucial to obtaining an accurate result.

For example, sensors for electrochemical fluid analysis applications (such as blood glucose testing) rely on proper fluid placement over electrodes, or "active" portions of the sensors. Fluid location is also important in an optically based sensor. If the fluid sample is not located within the light path, the system may yield an inaccurate result. Fluid placement within a sensor (for example, within a capillary cavity) thus becomes an important factor in achieving accurate measurements.

Many factors affect fluid placement within a sensor. For example, capillary geometry, internal capillary surface wettability, sample size, and composition all affect fluid placement. The impact of vent shape and location has been overlooked, as it pertains to fluid placement within a capillary-fill sensor. There is a need for fluid analysis sensors wherein the location and shape of vents are designed to effect proper fluid placement and thereby minimize required sample volume and increase accuracy of readings.

SUMMARY OF THE INVENTION

Sensors for fluid analysis are provided with one or more vents with various geometric shapes for directing fluid flow. Capillary action forces fluid into or through a fluid analysis sensor, and vent edges direct and control the flow of fluid through the sensor.

According to some embodiments of the invention, vent edges direct sample fluid to cover preferred portions of electrodes within a sensor.

Vent edges according to another embodiment of the invention are used to direct fluid along a tortuous path in a sensor.

According to another embodiment of the present invention, vents are used to control the timing of fluid flow through a sensor. Vents may further be used to control the timing of fluid contact with reagents.

The above summary of the present invention is not intended to represent each embodiment, or every aspect, of the present invention. Additional features and benefits of the present invention will become apparent from the detailed description, figures, and claims set forth below.

Figure 1:
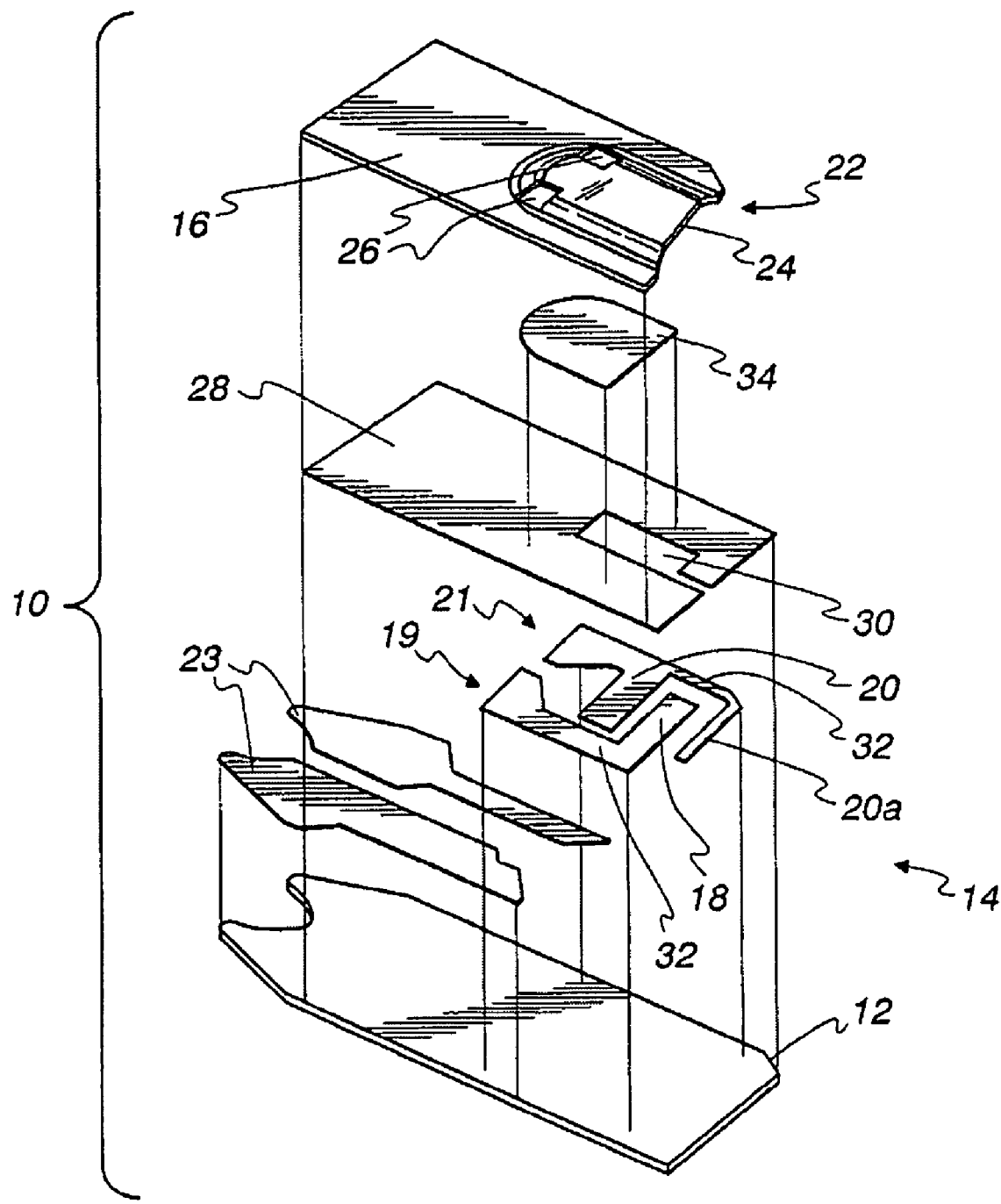
FIG. 1 is an exploded view of a fluid analysis sensor according to one embodiment of the present invention.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents and alternatives falling within the spirit and scope of the invention as defined by the appended claims.

DESCRIPTION OF ILLUSTRATED EMBODIMENTS

Sensors according to the present invention utilize vents to direct sample fluid toward desired testing locations, such as reagent areas and electrodes. Turning now to FIG. 1, a sensor 10 is shown in an exploded view. The sensor 10 comprises a base layer 12 for supporting sensor elements, an electrode layer 14, and a cover layer 16. The electrode layer 14 comprises first and second electrodes 18 and 20, both of which must make contact with a fluid sample to perform a test, such as blood glucose analysis, on the fluid sample. The electrodes 18 and 20 are contiguous with electrode assemblies 19 and 21 that make electrical contact with leads 23, allowing use of the sensor 10 in an electrochemical analysis device. The first and second electrodes 18 and 20 may also be termed, respectively, "working" and "counter" electrodes.

The second electrode assembly 21 is shown with a sub-electrode 20a that assists in detection of "underfill" situations when less than a required amount of sample fluid is inserted into the sensor 10. When the sensor 10 is underfilled with sample fluid, only a small amount of current will flow between the sub-electrode 20a and the first electrode 18, allowing for an alert to the user that the sensor 10 is underfilled.

The cover layer 16 overlays the electrode layer 14 and includes a fluid inlet area 22 into which fluid flows. The cover layer 16 further comprises a projection area 24 forming a sample cavity (shown in FIGS. 2 and 3, below) when the sensor 10 is assembled. First and second vents 26 are provided within the cover layer 16 for drawing fluid into the sample cavity via capillary action and further for guiding the placement of fluid within the sample cavity, as shown in greater detail in FIGS. 2 and 3. A dielectric layer 28 between the electrode layer 14 and the cover layer 16 surrounds a sample contact area 30 and assures that sample fluid does not make electrical contact with electrode leads 32 because contact with these leads 32 would result in inaccurate readings.

A reagent 34 is placed between the dielectric layer 28 and the cover layer 16 and contains chemicals that interact with sample fluid to produce desired electrochemical properties for analysis of the sample.

Figure 2:
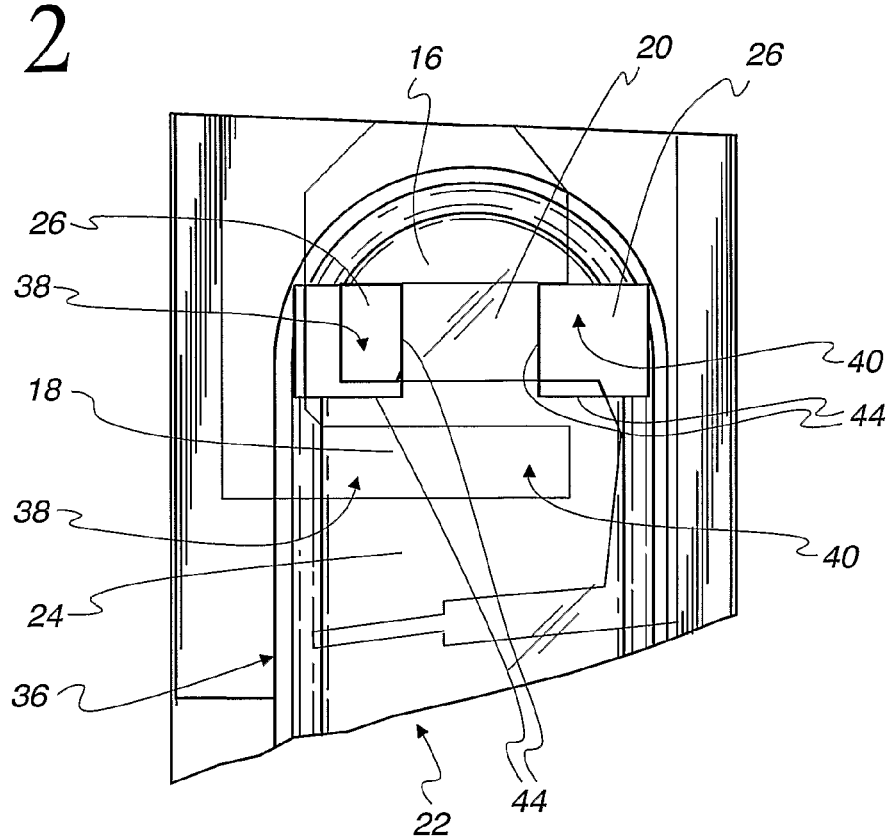
FIG. 2 is a front view of a fluid analysis sensor.

Turning now to FIG. 2, a front view of the sensor 10 of FIG. 1 focuses on a sample cavity 36 formed by the projection area 24 of the cover layer 16. The sample cavity 36 is designed to hold fluid for testing such that fluid contacts both the first electrode 18 and the second electrode 20 of the electrode layer 14. In practice, sample fluid enters the sample cavity 36 through the fluid inlet area 22 and is drawn into the sample cavity 36 via capillary action enabled by the vents 26. Sample fluid is held in contact with the first and second electrodes 18 and 20 and electrochemical testing, such as blood glucose testing, may be performed on the fluid sample.

The outer edges 38 and 40 of the electrodes 18 and 20 are covered by a dielectric layer as in FIG. 1, item number 28, and thus these edges are electrochemically inert. (For ease of illustration, the dielectric layer is not shown in FIG. 2.) It is desirable to direct sample fluid toward the center, active portions of the electrodes 18 and 20.

Figure 3:
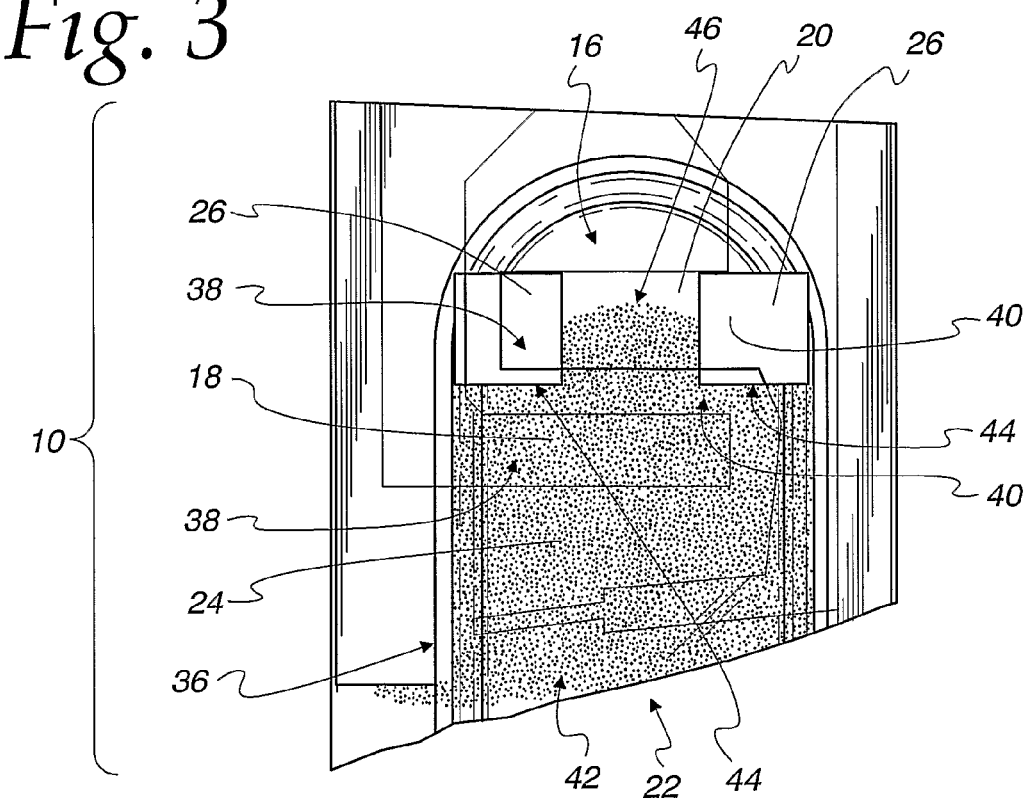
FIG. 3 is a front view of the fluid analysis sensor of FIG. 2 containing sample fluid within a sensor test cavity.

FIG. 3 shows a sensor 10 in the isometric view of FIG. 2 with sample fluid 42 within the sample cavity 36. Sample guide edges 44 of the vents 26 guide the sample fluid 42 away from the outer edges 38 and 40 of the counter electrode 20 and toward the middle of the electrode where optimum electrical contact between the sample fluid 42 and the electrodes 18 and 20 can be made. As shown in FIG. 3, a leading edge 46 of the sample fluid 42 has been guided between the vents 26 to make sufficient contact with the second electrode 20 to result in an accurate reading from the sensor 10.

Figure 4A:
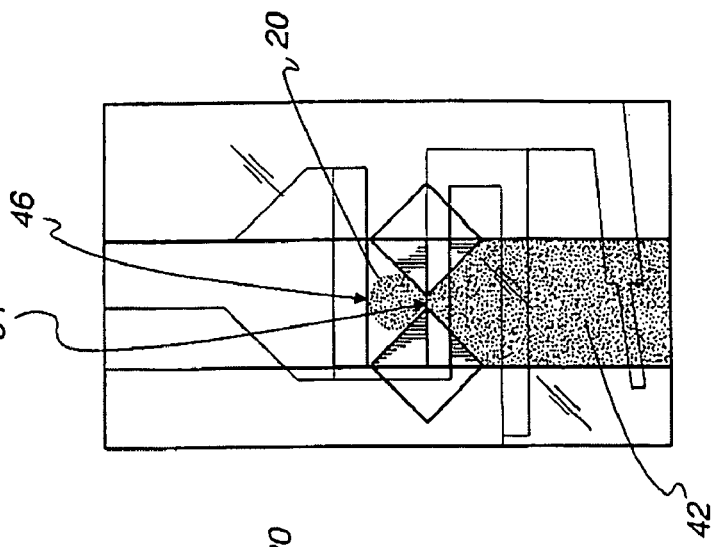
FIGS. 4a-4c are time elapse drawings showing the flow of sample fluid in a sensor.
Figure 4B:
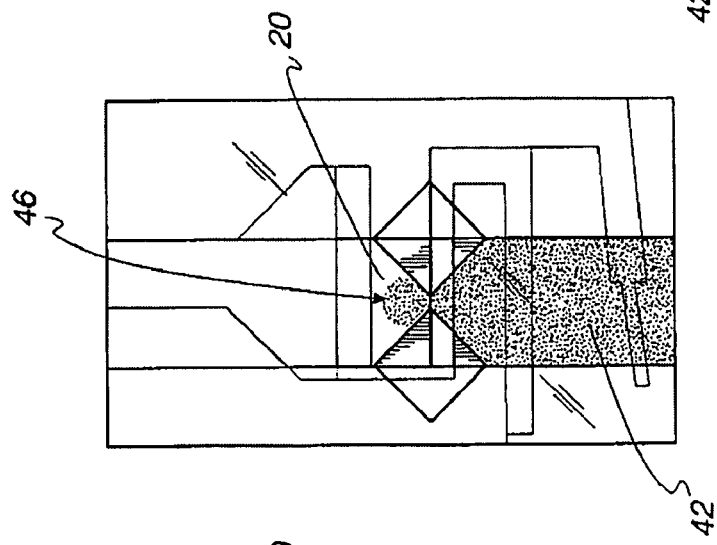
Figure 4C:
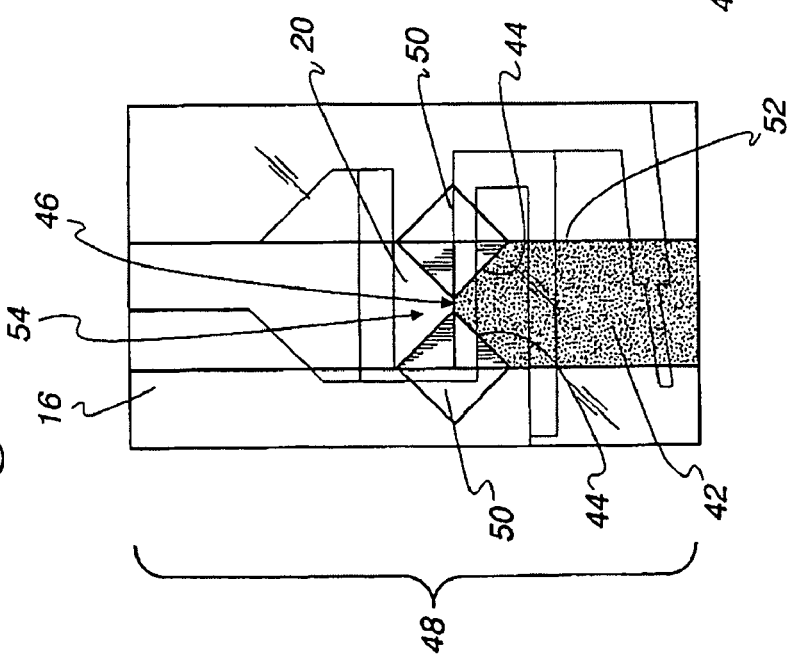

Sensors employing vents according to the present invention may be used in a variety of embodiments to improve fluid testing applications. FIGS. 4a-c are time-elapse images of a sensor 48 employing vents 50 to create a bottleneck or "pinch point" for sample fluid 42 as it flows through the sensor 48. As shown in FIG. 4a, the sample fluid 42 is first drawn into the sensor 48 via capillary action and restrained between spacer edges 52 beneath a cover layer 16. The leading edge 46 of the sample fluid 42 has followed sample guide edges 44 of the vents 50 into a bottleneck region 54. Though the vents 50 are square-shaped, they are angled such that the spacer edges 52 intersect opposing vertices of the vents 50, and the profiles of the vents 50 as presented to the sample fluid 42 are opposing right isosceles triangles. The sample fluid 42 is shown in FIG. 4a at a point just short of contacting the second electrode 20.

Turning now to FIG. 4b, the sensor 48 of FIG. 4a is shown at a later time. The leading edge 46 of the sample fluid 42 has progressed beyond the bottleneck region 54 of the sensor 48 and now a portion of the sample fluid 42 contacts a central area of the second electrode 20. The leading edge 46 continues past the bottleneck region 54 as time progresses, as shown in FIG. 4c, resulting in even more complete coverage of the second electrode 20 by the sample fluid 42. Vents having sample guide edges that result in a bottleneck region are useful for precise guiding of sample fluid within a sensor and for more precise timing control as fluid passes through the sensor, due to the slowing of the fluid by the bottleneck region. According to one embodiment, the progression shown in FIGS. 4a-c takes place over approximately three seconds, whereas without the bottleneck the progression would take less than 0.3 seconds.

Figure 5A:
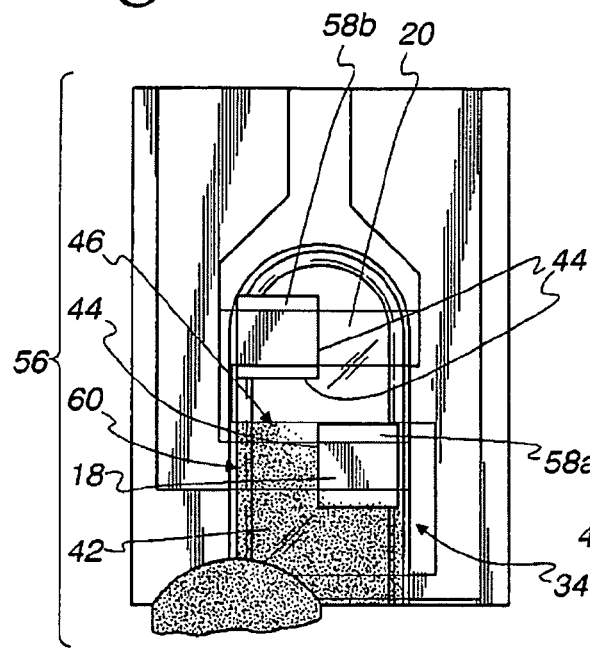
FIGS. 5a-5d are time elapse drawings showing the flow of sample fluid in another sensor.

Vents according to the present invention may be placed to cause sample fluid to flow along specific pathways and to delay fluid flow through a sensor. Such applications are useful to improve mixing between sample fluid and a reagent, and to more precisely control the timing of fluid flow through a sensor. FIGS. 5a-5d are time-elapse images of a sensor 56 having two vents 58a,b placed in staggered positions to create a tortuous path for sample fluid 42 to follow. FIG. 5a shows sample fluid 42 entering the sensor 56 and being led along a fluid pathway 60 by sample guide edges 44 of the vents 58a,b. In FIG. 5a, the sample fluid 42 recently entered the sensor 56 and has been guided across a first electrode 18 by the sample guide edges 44 of a first vent 58a. The leading edge 46 of the sample fluid 42 is between the first electrode 18 and the second electrode 20.

Figure 5B:
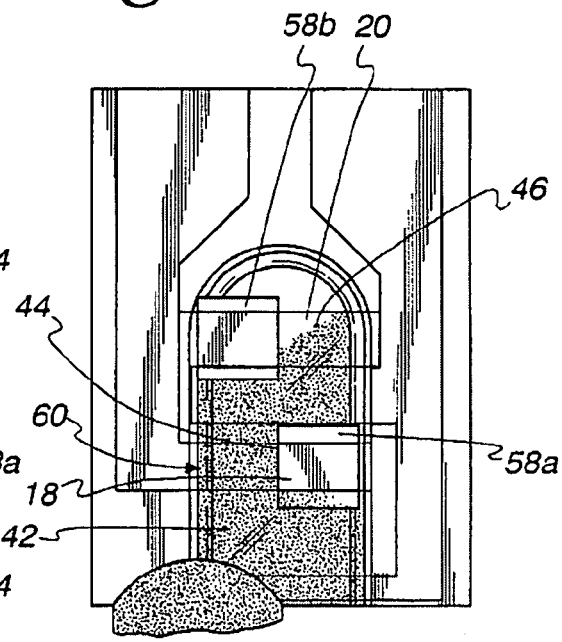
Figure 5C:
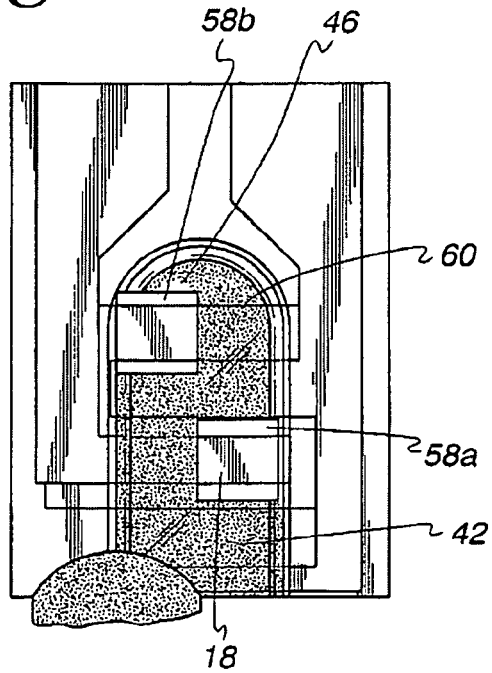
Figure 5D:
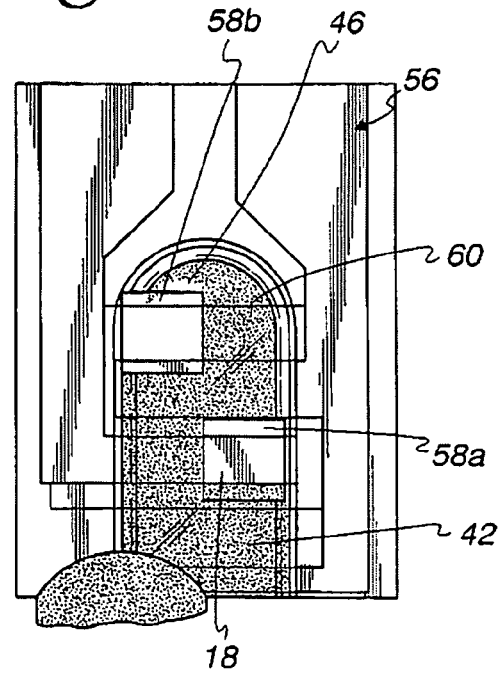

Later, as shown in FIG. 5b, the leading edge 46 of the sample fluid 42 has been guided around a second vent 58b by the sample guide edges 44 of the second vent 58b, and the sample fluid 42 is now making contact with the second electrode 20. The sample fluid 42 continues to flow through the sensor 56 as shown in FIGS. 5c and 5d, with the leading edge 46 continuing to follow the fluid pathway 60 as it progresses through the sensor 56.

Tortuous pathways such as the one shown in FIGS. 5a-5d result in additional mixing between sample fluid 42 and reagent 34 within the sensor 56 due to increased turbulence resulting from the turns of the sample fluid 42 along the fluid pathway 60. Further, significant time delays can result from the use of a tortuous fluid pathway 60. For example, a sensor 56 as shown FIGS. 5a-5d according to some embodiments allows for delays of one to five seconds between initial insertion of fluid into the sensor and complete progression of the sample fluid along the fluid pathway. The timing of fluid flow along the fluid pathway may be changed by narrowing or widening the pathway or by making the fluid pathway longer or shorter, for example by employing different sizes of vents 58a,b in different locations defining the fluid pathway.

Figures 6A, 6B, 6C:
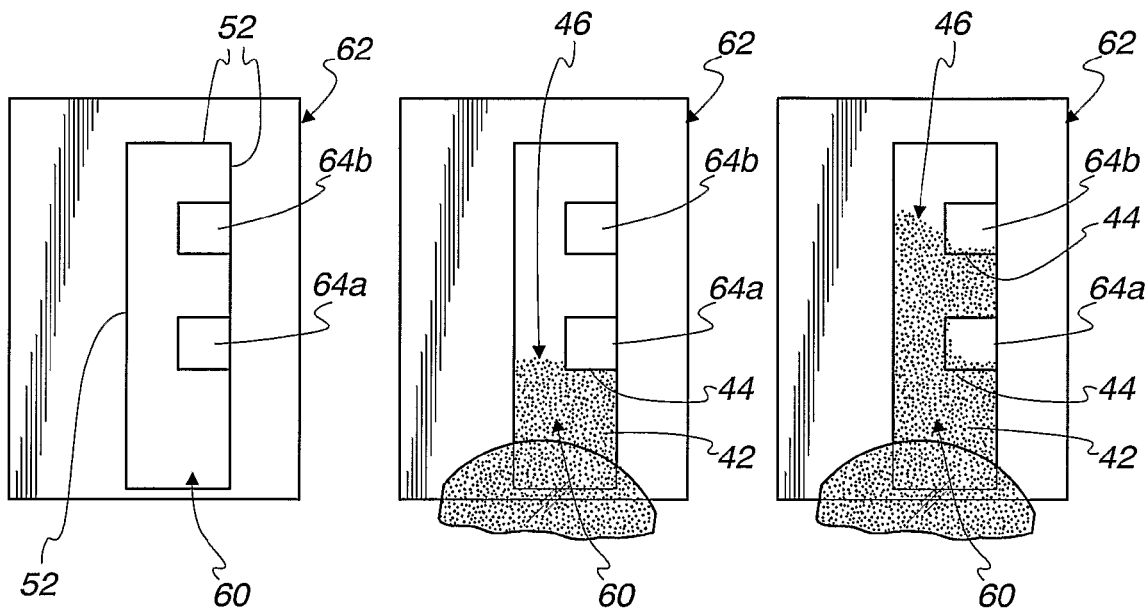
FIGS. 6a-6f are time elapse drawings showing the flow of sample fluid in yet another sensor.

Controlled timing of fluid flow through a sensor is beneficial when more than one reagent is used, with different reagents having different optimum reaction times with the sample fluid. Multiple reagents may be used in certain optical and electrochemical testing applications. Turning now to FIGS. 6a-f, a sensor 62 having first and second vents 64a and 64b to control timing of fluid flow along a fluid pathway 60 is illustrated in time-elapse images. FIG. 6a shows the sensor 62 before sample fluid has been introduced into the sensor 62. FIG. 6b shows sample fluid 42 being introduced into the sensor 62. The leading edge 46 of the sample fluid 42 is guided by sample guide edges 44 along the fluid pathway 60 around the first vent 64a. In FIG. 6c, the leading edge 46 of the sample fluid 42 has progressed past the first vent 64a and is being guided by the sample guide edges 44 of the second vent 64b.

Figures 6D, 6E, 6F:
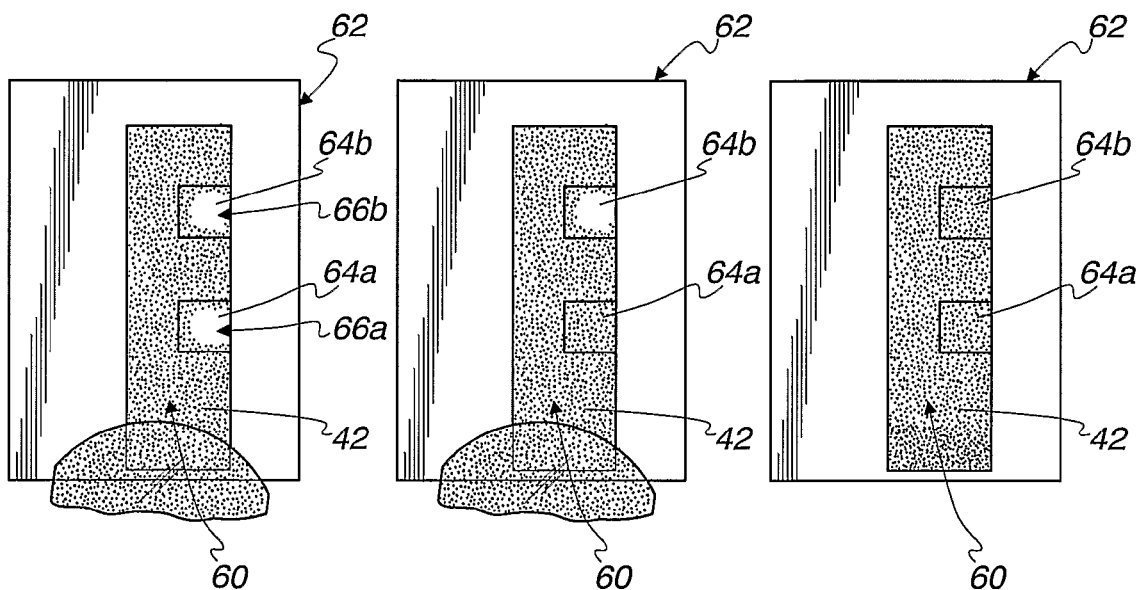

Turning now to FIG. 6d, the sample fluid 42 has filled in the fluid pathway 60 and is now bounded by the outer pathway edges (which in FIGS. 6a-6f are spacer edges 52) and the sample guide edges 44 of the vents 64a and 64b. Next, as shown in FIG. 6e, the sample fluid 42 fills in the volume beneath the first vent 64a. Finally, as shown in FIG. 6f, the sample fluid 42 fills in the volume beneath the second vent 64b. If reagent is supplied in two reagent areas 66a and 66b (as shown in FIG. 6d), the process shown in FIGS. 6a-6f may be used to control the timing of contact of the sample fluid 42 with each of the reagents.

The timing of sample fluid flow as shown in FIGS. 6a-6f is beneficial in applications such as blood and urine testing in which many analytes having different optimum reaction times may be used. For example, if a first reagent is placed in the first reagent area 66a and a second reagent is placed in the second reagent area 66b, the sample fluid 42 will begin to react with the first reagent before it reacts with the second reagent because the area of the first vent 64a is filled more quickly with sample fluid than is the area of the second vent 64b. As in the embodiments of FIGS. 4a-4c and 5a-5d, the length and width of the fluid pathway and the sizes and shapes of the vents may be changed to result in desired timing. According to some embodiments, timing delays of two to five seconds between contacts with reagent areas may be achieved by using the embodiment of FIGS. 6a-6f. Even longer delays can be envisioned by manipulating the surface properties, such as wettability, of the reagents.

The utility of such a delay might also be implemented in a scheme whereby the product of the first reagent zone diffuses to a second reagent zone and serves as a substrate for a second reaction. Because of the timing delay, the concentrations of both reaction products can be determined.

Another use of the embodiment of FIG. 6 would enable reading multiple reagent zones simultaneously by use of corresponding multiple signal transduction elements, including light beams and electrodes. In this embodiment, the differential wet-up time provides varying reaction times when all signal transducers are read simultaneously.

While the invention is susceptible to various modifications and alternative forms, specific embodiments thereof have been shown by way of example in the drawings and are described in detail herein. It should be understood, however, that it is not intended to limit the invention to the particular forms disclosed, but, to the contrary, the intention is to cover all modifications, equivalents and alternatives falling within the spirit and scope of the invention as defined by the appended claims.

What is claimed is:

1. A sensor for analysis of a fluid sample comprising:
   a sample cavity for accepting sample fluid;
   at least one test region disposed along said sample cavity; and
   at least one vent for venting said sample cavity, said at least one vent having at least one sample guide edge for guiding said sample fluid to said at least one test region.

2. The sensor of claim 1 having a plurality of vents having aligned sample guide edges for guiding said sample fluid toward said test region.

3. The sensor of claim 1 wherein said at least one vent comprises two staggered vents spaced from each other to form a fluid pathway within said sample cavity.

4. The sensor of claim 3 wherein said fluid pathway is a tortuous fluid pathway having at least one turn along which said sample fluid flows.

5. The sensor of claim 4 further comprising a reagent layer in communication with said sample cavity.

6. The sensor of claim 1 wherein said at least one test region is selected from the group consisting of an electrode and a reagent area.

7. The sensor of claim 1 wherein said at least one test region comprises two electrodes.

8. The sensor of claim 7 further comprising a dielectric material covering edges of said two electrodes.

9. A sensor for analysis of a fluid sample comprising:
   a sample cavity for accepting sample fluid;
   at least one test region disposed along said sample cavity; and
   at plurality of vents for venting said sample cavity, said plurality of vents having aligned sample guide edges for guiding said sample fluid toward said at least one test region,
   wherein two vents are square-shaped and wherein said test region is located between sample guide edges provided on separate zones of said two vents.

10. A sensor for analysis of a fluid sample comprising:
    a sample cavity for accepting sample fluid;
    at least one test region disposed along said sample cavity; and
    at least one vent for venting said sample cavity, said at least one vent having at least one sample guide edge for guiding said sample fluid to said at least one test region;
    wherein said at least one vent comprises two vents being placed proximate to each other to form a bottleneck region for controlling a flow of said sample fluid.

11. A method for collecting sample fluid and positioning sample fluid in a test sensor for analysis of said sample fluid the method comprising the acts of:
    accepting said sample fluid within a sample cavity via capillary action; and
    directing said sample fluid through said sample cavity toward at least one test region of said sensor using at least one sample guide edge provided on at least one vent venting said sample cavity.

12. The method of claim 11 wherein accepting said sample fluid comprises accepting said sample fluid at a fluid inlet area.

13. The method of claim 11 wherein said at least one test region is selected from the group consisting of an electrode and a reagent area.

14. The method of claim 11 wherein said at least one test region comprises two electrodes.

15. The method of claim 11 wherein said at least one vent comprises two vents.

16. The method of claim 15 wherein said two vents are placed at staggered positions within along said sample cavity and further comprising directing said sample fluid along a fluid pathway.

17. The method of claim 16 wherein said test sensor is provided with a reagent disposed along said sample cavity, wherein said fluid pathway is tortuous, and further comprising mixing said test fluid with said reagent as said sample fluid is directed along said fluid pathway.

18. A sensor for analysis of a fluid sample comprising:
    a sample cavity for accepting sample fluid, said sample cavity having an fluid inlet;
    first and second vents within said sample cavity, said first and second vents having respective first and second vent edges and being disposed along a fluid pathway of said sample cavity such that said first vent is closer to said fluid inlet than said second vent is;
    a first reagent area disposed along said sample cavity beneath said first vent; and
    a second reagent area disposed along said sample cavity beneath said second vent
    wherein said first vent edge and said second vent edge guide said fluid sample along said fluid pathway.

19. The sensor of claim 18 wherein said first and second vents are spaced along said fluid pathway such that sample fluid entering said fluid inlet contacts said first and second vent edges in succession.

20. The sensor of claim 18 wherein said first reagent is adapted to react with said sample fluid for a first optimum reaction time and said second reagent is adapted to react with said sample fluid for a second optimum reaction time, said second optimum reaction time being less than said first optimum reaction time.

21. The sensor of claim 18 further comprising additional vents having vent edges and being disposed along said fluid pathway.

22. The sensor of claim 21 further comprising additional reagent areas disposed along said sample cavities respectively beneath said additional vents.

23. A method for analyzing a fluid sample comprising:
    accepting said sample fluid within a sample cavity via capillary action, said sample cavity having a fluid inlet and first and second vents disposed along a fluid pathway, said sample cavity further having a first reagent disposed beneath said first vent and a second reagent disposed beneath said second vent, said first and second vents having first and second vent edges;

guiding said fluid sample along said fluid pathway via capillary action such that said fluid passes said first vent before passing said second vent; and filling said sample cavity such that said sample fluid first fills a first volume beneath said first vent and later fills a second volume beneath said second vent wherein said first vent edge and said second vent edge guide said fluid sample along said fluid pathway.

24. The method of claim 23 wherein a time delay between the time at which said sample fluid fills said first volume beneath said first vent and the time at which said sample fluid fills said second volume beneath said second vent is greater than about three seconds.

25. A sensor for analysis of a fluid sample comprising:

a base layer;

an electrode layer supported by said base layer, said electrode layer having a first electrode and a second electrode, said first and second electrodes respectfully extending from first and second electrode leads and having central portions;

a cover layer disposed above said electrode layer, said cover layer having a projection defining a sample cavity;

a fluid inlet area in fluid communication with said sample cavity; and first and second vents, said first vent having a first sample guide edge and said second vent having a second sample guide edge opposing said first sample guide edge, said first and second sample guide edges opposing each other above at least one of said central portions of said first and second electrodes, said first sample guide edge and said second sample guide edge guiding said fluid sample along a fluid pathway of said sample cavity.

26. The sensor of claim 25 wherein said first and second electrodes have central portions, an intermediate area between said first and second opposing guide edges being disposed above one of said central portions of said electrodes.

27. A sensor for analysis of a fluid sample comprising:

a sample cavity having a fluid inlet area, said sample cavity adapted for being filled via capillary action and having a vent, said vent having at least one sample guide edge for guiding fluid under capillary action within said sample cavity during filling of said sample cavity.

28. A method for determining an analyte concentration of a fluid sample comprising the acts of:

providing a test sensor having at least one vent, said at least one vent having at least one sample guide edge;

accepting said fluid sample within a sample cavity, said sample cavity having a fluid inlet;

guiding said fluid sample along a fluid pathway such that said sample fluid is directed by said at least one sample guide edge to at least one test region; and determining said analyte concentration in said sample fluid.

29. The method of claim 28 wherein the test sensor includes at least two vents.

30. A sensor for analysis of a fluid sample comprising:

a base layer;

first and second electrodes respectfully extending from first and second electrode leads and each having central portions;

a cover layer in which said cover layer assists in defining a sample cavity;

a fluid inlet area in fluid communication with said sample cavity; and first and second vents, said first vent having a first sample guide edge and said second vent having a second sample guide edge, said first and second sample guide edges being located to assist in guiding said fluid sample to at least one test region.

* * * * *